United States Patent [19]

Greenstein

[11] Patent Number: 5,681,744

[45] Date of Patent: Oct. 28, 1997

[54] DELIVERY AND EXPRESSION OF HETEROLOGUS GENES USING UPSTREAM ENHANCER REGIONS OF MAMMALIAN GENE PROMOTERS

[76] Inventor: Robert J. Greenstein, 73 Windsor Rd., Tenafly, N.J. 07670-2615

[21] Appl. No.: 405,600

[22] Filed: Mar. 17, 1995

[51] Int. Cl.[6] .................... C12N 15/85; C12N 15/63; C07H 21/04; C12P 21/02
[52] U.S. Cl. .................. 435/320.1; 435/69.1; 536/24.1
[58] Field of Search ........................ 435/320.1, 69.1; 536/24.1

[56] References Cited

U.S. PATENT DOCUMENTS 5,476,926 12/1995 Spiegelman et al. .................. 536/24.1
5,486,462 1/1996 Rutter et al. ........................... 435/69.1

FOREIGN PATENT DOCUMENTS

WO9307280 4/1993 WIPO ......................... C12N 15/85

OTHER PUBLICATIONS

Devine-Beach et al., Analysis of the proximal transcriptional element of the myelin basic protein gene, Nucleic Acids Res. 20(3):545–550 Feb. 11, 1992.
Agnati et al., "Evidence for Cholecystokinin–Dopamine Receptor Interactions in the Central Nervous System of the Adult and Old Rat," (1985) Ann. NY Acad. Sci..
Bancroft et al., "Control of the Production of Two Protein Hormones by Rat Pituitary Cells in Culture," (1970) In Vitro 6:180–189.
Beato et al., "DNA Regulatory Elements for Steroid Hormones," (1989) J. Steroid Biochem. 32:737–747.
Cato et al., "Different Regions of hte Estrogen Receptor are Required for Synergisic Action with the Glucocorticoid and Progesterone Receptors," (1989) Mol. Cell Biol. 9:5324–5330.
Dahlman-Wright et al., "DNA–Binding by the Glucocorticoid Receptor: A Structural and Functional Analysis," (1992) J. Steroid Biochem. Mol. Biol. 41:249–272.

Danesch et al., "Glucocorticoid Induction of the Rat Tryptophan Oxygenase Gene is Medicated by Two Widely Separated Glucocorticoid–Responsive Elements," (1987) EMBO J. 6:625–630.
Deschenes et al., "Cloning and Sequence Analysis of a cDNA Encoding Rat Preprocholecystokinin," (1984) Proc. Nat'l Acad. Sci. USA 81:726–730.
Dockray, G.J., "Immunochemical Evidence of Cholecystokinin–like Peptides in Brain," (1976) Nature 264:568–570.
Friedman et al., "Differential Expression of hte Mouse Cholecystokinin Gene During Brain and Gut Development," (1985) Proc. Nat'l Acad. Sci. USA 82:5593–5597.
Greenstein, R.J., "The Brain–Gut Axis: A Model System to Study Gene Regulation," (1992) Mt. Sinai J. Med. 59:135–138.
Greenstein et al., "Is Aging Preprogrammed? Observations from the Brain/Gut Axis," (1991) Mech. Aging Dev. 61:113–121.
Greenstein et al., "Cholecystokinin Upregulation during Intestinal Repair," (1992) J. Surg. Res. 53:12–16.
Haun et al., "Transcriptional Enhancer Essential for the Expression of the Rat Cholecystokinin Gene Contians a Sequence Identical to the –296 Development of the Human c–fos Gene," (1990) J. Biol. Chem. 265:15455–15463.
Ichihara et al., "Ontogeny of Immunoreactive CCk, VIP and Secretin in Rat Brain and Gut," (1983) Biochem. Biophys. Res. Comm. 112:891–898.

(List continued on next page.)

Primary Examiner—Nancy Degen
Attorney, Agent, or Firm—Law Offices of Jane Massey Licata

[57] ABSTRACT

DNA vectors containing an effective upstream enhancer region of a tissue or organ specific mammalian promoter of an endogenous gene and a selected gene useful in delivery of the selected gene to a tissue or organ of an animal are provided. A method for evaluating the efficacy of agents in facilitating transfection is also provided.

1 Claim, 9 Drawing Sheets

OTHER PUBLICATIONS

Konings et al., "Processing, Release and Metabolism of Cholecystokinin in SK–N–MCIXC Cells," (1993) *Neuropeptides* 25:19–30.

Moore et al., "The First Intron of the Human Growth Hormone Gene Contains a Binding Site for Glucocorticoid Receptor," (1985) *Proc. Natl. Acad. Sci. USA* 82:699–702.

Monstein, H.J., "Identification of an AP–1 Transcription Factor Binding Site within the Human Cholecystokinin (CCK) Promoter," (1993a) *Neuroreport.* 4:195–197.

Monstein, H.J., "Modulated Cholecystokinin (CCK) mRNA Expression is Dependent on de novo Protein Synthesis," (1993b) *Neuroreport.* 4:1167–1170.

Muller et al., "Cholecystokinin and its COOH–Terminal Octapeptide in the Pig Brain," (1977) *Proc. Nat'l Acad. Sci. USA* 74:3035–3037.

Oro et al., "Estrous Cycle Variations in Levels of Cholecystokinin Immunoreactivity within Cells of Three Interconnected Sexually Dimorphic Forebrain Nuclei," (1988) *Neuroendocrinology* 47:225–235.

Slater et al., "Glucocortincoid Receptor Binding and Activation of a Heterologo Promoter by Dexamethasone by the First Intron of the Human Growth Hormone Gene," (1985) *Mol. Cell. Biol.* 5:2984–2992.

Simerly et al., "Castration Reversable Alters Levels of Chlecystokinin Immunoreactivity within Cells of Three Interconnected Sexually Dimorphic Forebrain Nuclei in the Rat," (1987) *Proc. Nat'l Acad. Sci. USA* 84:2087–2091.

Tashjian et al., "Establishment of Clonal Strains of Rat Pituitary Tumor Cells the Secrete Growth Hormone," (1968) *Endocrinology* 82:342–352.

Truss et al., "Functional Interaction of Hybrid Response Elements with Wild–Type and Mutant Steroid Hormone Receptors," (1991) *Mol. Cell Biol.* 11:3247–3258.

Vanderhaegen et al., "New Peptide in the Vertebrate CNS Reacting with Antigastrin Antibodies," (1975) *Nature* 257:604–605.

Zhang et al., "Positional Cloning of the Mouse obese Gene and its Human Homologue," (1995) *Nature* 372:425–432.

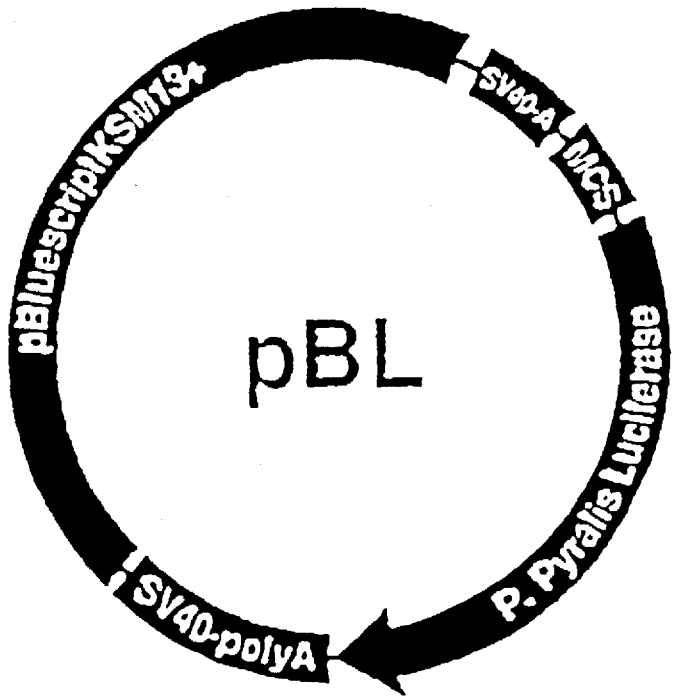

Plasmids construct.

| Construct | Multiple Cloning Site (MCS) Insert |
|---|---|
| pBL-luc | none (basic construct) |
| pBLTK-luc | Herpes Simplex Virus Thymidine Kinase Promoter (TK) |
| pRSV-luc | Rous Sarcoma virus (RSV) |
| pSV40-luc | Simian V-40 (SV40) |
| pCMV-luc | Cytomegalovirus (CMV) |
| pCMV-Gal | Cytomegalovirus (CMV) and ß-galactosidase reporter gene |
| pCCK UER-Luc | CCK UER (-400 +73) |
| pBL015D-Luc | Rat genomic DNA fragment, PCR artifact (8% homology with CCK UER, 560 b.p.) |

FIGURE 2

DELIVERY AND EXPRESSION OF HETEROLOGUS GENES USING UPSTREAM ENHANCER REGIONS OF MAMMALIAN GENE PROMOTERS

FIELD OF THE INVENTION

This invention relates to the field of tissue specific promoters of gene expression and specifically in their use as gene delivery vectors that can deliver genes to any tissues to yield regulated gene expression. It also relates to a gene transplantation strategy that capitalizes on the use of tissue or organ specific promoters that normally regulate endogenous gene products in a tissue or organ to reintroduce foreign genes under the same regulatory mechanisms in a target tissue or organ.

The present invention also relates, but is not limited, to gene transplantation in the gut by oral or enteral methods or in the brain by intracerebroventricular or direct delivery.

The present invention further relates to development of model systems to delineate and discover additional transcriptional enhancers or inhibitors of eukaryotic promoters in the context of a cellular environment wherein appropriate endogenous regulatory mechanisms of the promoter of interest reside.

In addition, the present invention relates to model promoter reporter systems that can be used in the evaluation of compounds that increase transfectional efficiency which may be advanced as gene transfer agents in gene therapeutic approaches.

BACKGROUND OF THE INVENTION

Regulation of eukaryotic gene expression involves the interaction of transcriptional factors with specific DNA sequences. For example, in genes responsive to steroid hormones, precise transcriptional regulation is achieved when steroid hormones and their receptor-complex bind to well characterized palindromic DNA sequences (Dahlman-Wright, K. et al. (1992) *J. Steroid Biochem. Mol. Biol.* 41:249–272). Such regions, termed hormone responsive elements (HRE's), are found at variable distances upstream of promoters as well as occasionally within introns (Danesch, U. etal. (1987) *EMBO J.* 6:625–630; Slater, E. P. et al. (1985) *Mol. Cell Biol.* 5:2984–2992; Moore, D. D. et al. (1985) 82:699–702). HRE's are classified into two subgroups: glucocorticoid/progesterone responsive elements (GRE/PRE), which are regulated by glucocorticoids, androgens, gestagens and mineralocorticoids (Beato, M. et al. (1989) *J. Steroid Biochem.* 32:737–747) and estrogen responsive elements (ERE) which mediate the effect of estrogens, thyroid hormones, vitamin D and vitamin A (retinoic acid) (Truss, M. et al. (1991) *Mol. Cell Biol.* 11:3247–3258). These genes and their promoters are found selectively or specifically on certain tissues and thus confer tissue specific gene expression which is regulated by the cognate hormones.

Cholecystokinin (CCK) is a prototypical brain-gut peptide (Ichihara, K. et al. (1983) *Biochem. Biophys. Res. Comm.* 112:891–898; Freidman et al. (1985) *Proc. Natl. Acad. Sci. USA* 82:5593–5597; Ivy, A. C. and Oldberg, E. (1928) *Am. J. Physiol.* 86:599–613; Vanderhaegen, J. J. et al. (1975) *Nature* 257:604–605; Dockray, G. J. (1976) *Nature* 264:568–570) that has hemacrine (Ivy, A. C. and Oldberg, E. (1928) *Am. J. Physiol.* 86:599–613; Muller, J. E. et al. (1977) *Proc. Nat'l Acad. Sci. USA* 74:3035–3037) and autocrine (Greenstein, R. J. et al. (1992) *J. Surg. Res.* 53:12–16) action in the gut, but is a neurotransmitter in the brain (Agnati, L. F. et al. (1985) *Ann. N.Y. Acad. Sci.* 448:315–333; Konings, P. N. et al. (1993) *Neuropeptides* 25:19–30). Gonadal steroids regulate neural CCK expression in the adult rat (Simerly, S. B. and Swanson, L. W. (1987) *Proc. Nat'l Acad. Sci. USA* 84:2087–2091). The 119 bp 5' flanking region of the rat CCK gene contains a cAMP-responsive region (5' CAP site) homologous to the human c-fos receptor region as well as a TPA-responsive element (Haun, R. S. and Dixon, J. E. (1990) *J. Biol. Chem.* 265:15455–15463). The same region additionally contains a sequence which induces expression in both a position and an orientation independent manner (Haun, R. S. and Dixon, J. E. (1990) *J. Biol. Chem.* 265:15455–15463). CCK has been used to study tissue-specific gene expression (Greenstein, R. J. (1992) *Mt. Sinai J. Med.* 59:135–138; Greenstein, R. J. et al. (1991) *Mech. Aging Dev.* 61:113–121; Ichihara, K. et al. (1983) *Biochem. Biophys. Res. Commun.* 112:891–898; Friedman, J. et al. (1985) *Proc. Nat'l Acad. Sci. USA* 82:5593–5597; Monstein, H. J. (1993a) *Neuroreport.* 4:195–197; Monstein, H. J. (1993b) *Neuroreport.* 4:1167–1170; Haun, R. S. and Dixon, J. E. (1990) *J. Biol. Chem.* 265:15455–15463). However, its transcriptional regulation is not completely understood.

It has now been found that the intact CCK UER is a more powerful promoter than RSV, SV40 and herpes simplex thymidine kinase promoters and is exceeded only by the CMV promoter. DNA vectors comprising the effective upstream enhancer regions of tissue or organ specific mammalian promoters of endogenous genes provide an effective means for delivering foreign genes to a tissue, preferably in a tissue specific and differentially regulated manner.

SUMMARY OF THE INVENTION

The present invention relates to the utilization and construction of DNA vectors containing the effective upstream enhancer regions of tissue or organ specific mammalian promoters for expression of selected genes in a tissue. Methods of delivering these vectors are also provided.

In one embodiment, the effective upstream enhancer region (UER) is that of mammalian cholecystokinin (CCK) gene promoter. The intact 400 bp CCK-promoter has 20% the activity of the most powerful vital promoter used in gene transplantation, the cytomegalovirus (CMV) promoter, but is stronger than the simian virus (SV40) or herpes thymidine kinase (TK) promoters. Plasmid vector constructs containing reporter genes downstream of the CCK UER were maximally transfected into a rat pituitary cell line (GH3) with 14-carbon fully saturated acid lipids. These genes were shown to respond appropriately to cognate inducers of the CCK UER in GH3 cells. Furthermore, successful transfection, differential expression and reporter gene quantification of CCK UER or CCK-130 (a 3' truncated UER) driven plasmids were demonstrated in a rat model of enteral gene transplantation. In the gut, where endogenous CCK is produced and regulated, reporter gene expression was detected as far as the mid small bowel distal to injection site in the proximal duodenal wall or lumen. By contrast, in the liver where no endogenous CCK is produced or regulated, reporter gene expression was detected only at the liver injection site. This indicates that luminally transported DNA is successfully transfected and suggests that enteral, liposome transfected, eukaryotic regulated DNA transfer can be achieved with this method.

The present invention also provides a method for evaluating the efficacy of a selected agents in enhancing transfection which comprises transfecting a DNA vector containing an effective upstream enhancer region of a tissue or organ specific mammalian promoter of an endogenous gene and a selected gene with a selected agent into a selected cell line and comparing the levels of expression of the selected gene for each selected agent.

BRIEF DESCRIPTION OF THE FIGURES

FIG. 2 is a diagram of the plasmid construct with the upstream and downstream SV40 poly A stop codons, the luciferase reporter and the multiple cloning site (MCS). Tabulated beneath are each of the plasmid constructs which were evaluated.

In FIG. 5A luciferase expression of pCCK UER-luc was evaluated in the presence of calf serum (A), charcoal stripped calf serum (B), DMEM medium (C) and charcoal stripped DMEM medium (D). In FIG. 5B, luciferase expression of pCMV-luc was evaluated in the presence of calf serum (A), charcoal stripped calf serum (B), DMEM medium (C) and charcoal stripped DMEM medium (D).

FIG. 7B shows luciferase activity expressed by pCCK UER-50; FIG. 7C shows luciferase activity expressed by pCCK UER-130; FIG. 7D shows luciferase activity expressed by pCCK UER-140; and FIG. 7E shows luciferase activity expressed by pCCK UER-210. Ligands and their lanes are identical in each graph. Lane 1 is CCK UER expressed as 100%. Lane 2 is the deleted construct used in each graph as its own unstimulated control. Lane 3 is androstenedione; Lane 4 is 17β-estradiol; Lane 5 is progesterone; Lane 6 is corticosterone; and Lane 7 is aldosterone. All steroids are at 1 nM concentration. Lane 8 is TPA and Lane 9 is forskolin (both at 100 nM).

DETAILED DESCRIPTION OF THE INVENTION

Figure 1:
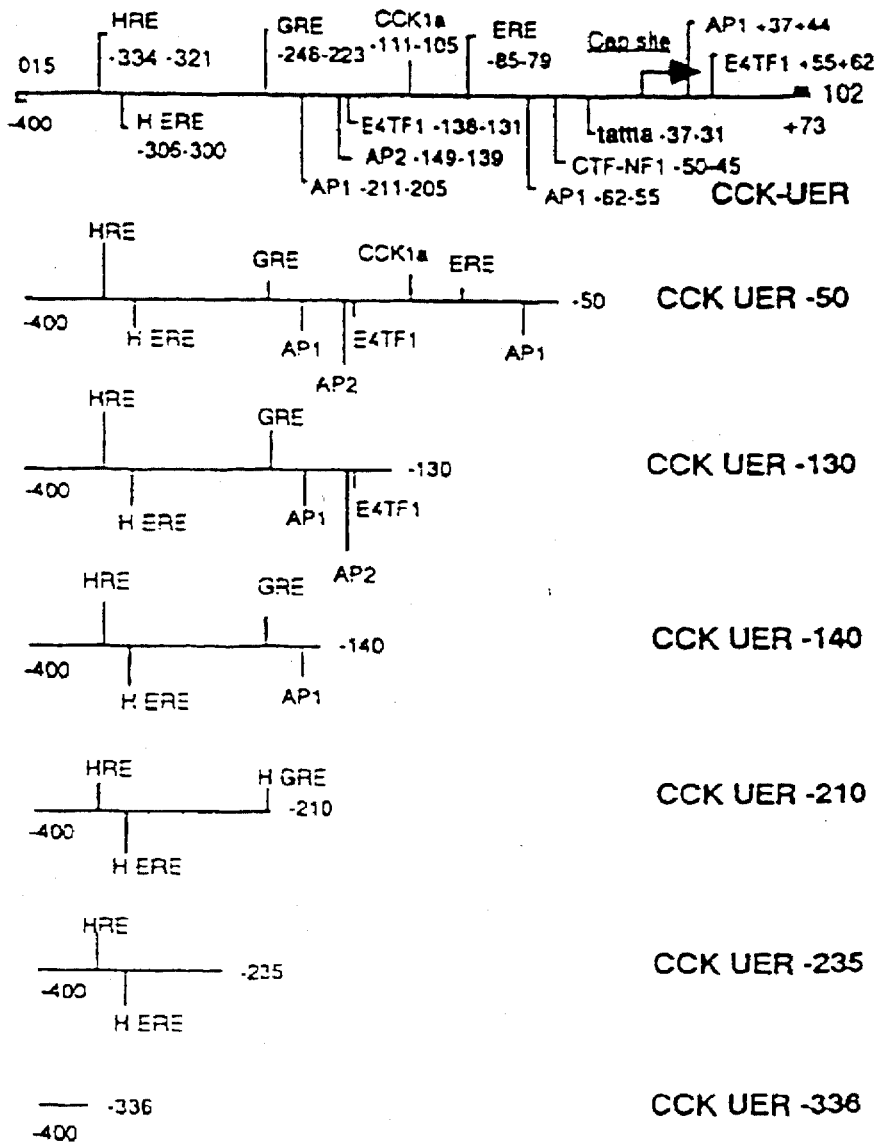
FIG. 1 is a map of CCK UER and its nested deletions. Binding sites for transcription factors are indicated on the upper line which shows the intact CCK UER. Location of the two primers (015 upstream and 102 downstream) are shown. The nested deletions constructs used are shown in FIG. 2. The number on the right in each construct designation indicates how far 5' to the CAP site the digestion has proceeded.

Gene therapy attempts to correct diseases by inserting missing or malfunctioning genes into an animal. The replacement gene is transplanted into the recipient where it will produce the desired product. However, delivering a gene specifically to a target tissue to have it appropriately and stably expressed and regulated for a therapeutically relevant time has proven to be somewhat difficult. Easy modes of administering these genes have also proven difficult. Oral gene delivery has proven especially difficult as well as non-invasive delivery of genes to the brain across the blood-brain barrier.

The present invention provides a method for delivering a selected gene to a tissue or organ using a DNA vector comprising an endogenous promoter and a selected gene. In a preferred embodiment, the present invention provides a method for delivering a selected gene to a specific target tissue or organ with a DNA vector comprising a promoter endogenous to the specific target tissue or organ. DNA vectors comprising endogenous tissue or organ specific promoters are also provided. In one embodiment, the present invention provides a method for transplanting genes by an oral or intraintestinal route into normal intestinal mucosal cells to obtain regulated expression and secretion of the desired gene products into the bloodstream with a DNA vector that comprises promoters endogenous to gut gene products. DNA vectors comprising brain-gut peptide promoters are also provided which can be used to enhance regulated tissue specific delivery in the brain. In other embodiments, the vector can be used to deliver a selected gene to a cell which does not contain this promoter, such as the liver. In one embodiment, the DNA vector comprises the brain/gut peptide upstream regulatory region of the cholecystokinin gene. However, other brain/gut promoters such as gastrin, somatostatin, vasoactive intestinal polypeptide (VIP) and neuropeptide Y (NPY) gene promoters may also be used. In addition, as will be appreciated by those of skill in the art, promoters for tissues or organs other than the brain or gut, can also be incorporated into the vector of the present invention for gene delivery. In a preferred embodiment, such promoters are selected to provide a gene delivery system selective for these other tissues or organs.

DNA vectors of the present invention may be administered by various routes including, but not limited to, intravenous or intraperitoneal injection, intratracheally, intrathecally, parenterally, intraarticularly and intramuscularly. Appropriate routes may be routinely selected by those of skill in the art based upon the particular tissue or organ to be targeted. In in vivo treatments, the DNA vectors of the present inventions are administered to an animal, particularly an animal having symptoms of a genetically-based disorder. Thus, the present invention is useful in a variety of animals including, but not limited to, domestic animals, feed stock such as bovine, ovine, and porcine, as well as primates, particularly humans. The amount of vector administered will be an amount sufficient to provide for a therapeutic level of transcription and/or translation in transfected cells. By therapeutic level of transcription and/or translation it is meant an amount sufficient to prevent, treat or palliate a disease in the treated animal following administration of the DNA vector. Accordingly, the dose of DNA vector administered should be sufficient to effectively treat, i.e., cause alleviation or reduction of symptoms, to inhibit the worsening of symptoms, to prevent the onset of symptoms, and the like. Dosages for the present invention which constitute a sufficient amount can be determined routinely by one of skill in the art upon this disclosure by performing routine trials with appropriate controls. Comparison of the appropriate treatment groups to the controls will indicate whether a particular dosage is effective in preventing or reducing particular symptoms. In addition to a tissue or organ specific promoter, the DNA vectors of the present invention also comprise a selected gene for delivery. By "selected gene" it is meant a gene encoding a bioactive substance which is chosen for transplantation into cells so that these cells will encode the bioactive substance. Examples of possible genes which may be selected include, but are not limited to, insulin, bioactive cytokines such as interleukin 1-β, tumor necrosis factor or the recently identified gene product associated with obesity (Zhang, Y. et al. (1995) *Nature* 372:425-432).

The rat CCK upstream enhancer region (UER) was cloned and a *Photinus pyralis* luciferase/CCK reporter plasmid constructed containing both the full length and a series of 3' deletions of the CCK UER. The full length CCK UER spans 473 bp beginning -400 bp 5' to the CAP site and ending +73 bp into the first exon of the rat CCK gene (see FIG. 1). This cloned sequence has 99.2% homology with the published CCK gene sequence (Deschenes, R. J. et al. (1984) *Proc. Nat'l Acad. Sci. USA* 81:726-730). There are two base deletions (c at -378 and g at -250), one base insertion (a at -239) and one base mismatch (c to g at -304). These constructs were transiently transfected into rat pituitary GH3 tumor cells (Tashjian, A. H. et al. (1968) *Endocrinology* 82:342-352). These cells express steroid receptors (Bancroft, F. C. and Tashjian, A. H. (1970) *In Vitro* 6:180-189), process CCK, and synthesize CCK mRNA thereby modeling the steroid regulatory mechanisms of CCK expression.

Using this reporter system, an optimal liposomal transfection formulation was determined and the transcriptional potency of CCK UER was compared with established vital promoters. The efficiency of 8 lipid compounds in transfecting the CCK UER luciferase reporter gene into GH3 cells was monitored by luciferase expression as measured by luminescence. Of all the compounds tested, transfection into GH3 cells is maximal when the hydrocarbon tail of the polar lipid has 14 fully saturated carbon atoms as in 1,2-dimyristoyl-sn-glycero-3-ethyphosphocholine (DMePCh) and 1,2-dimyristoyl-3-trimethylammonium-propane (DMTAPr).

Figure 5A:
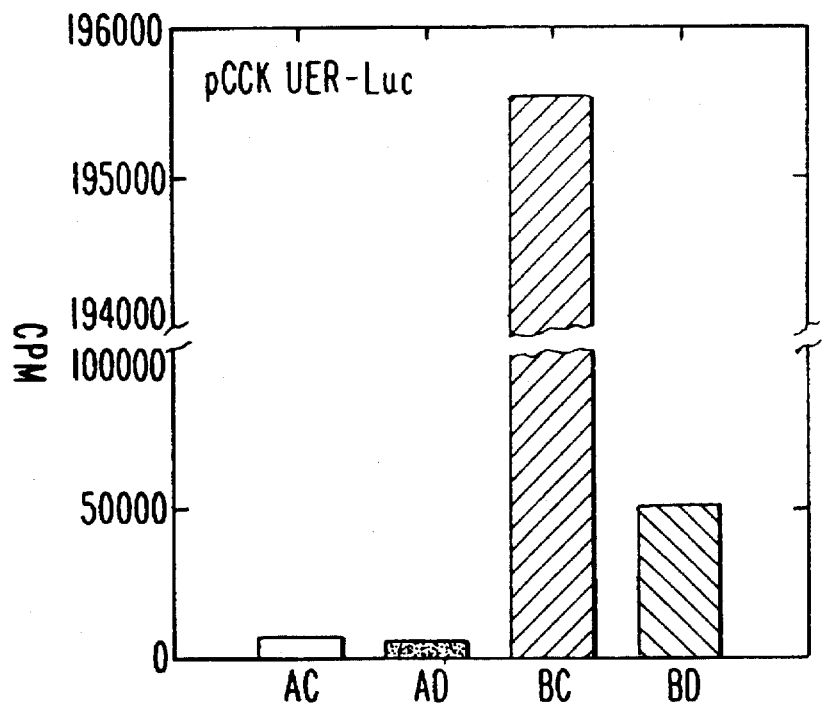
FIGS. 5A and 5B provide bargraphs showing luciferase expression in the presence of various constituents of the medium to determine which constituents effect the expression.
Figure 5B:
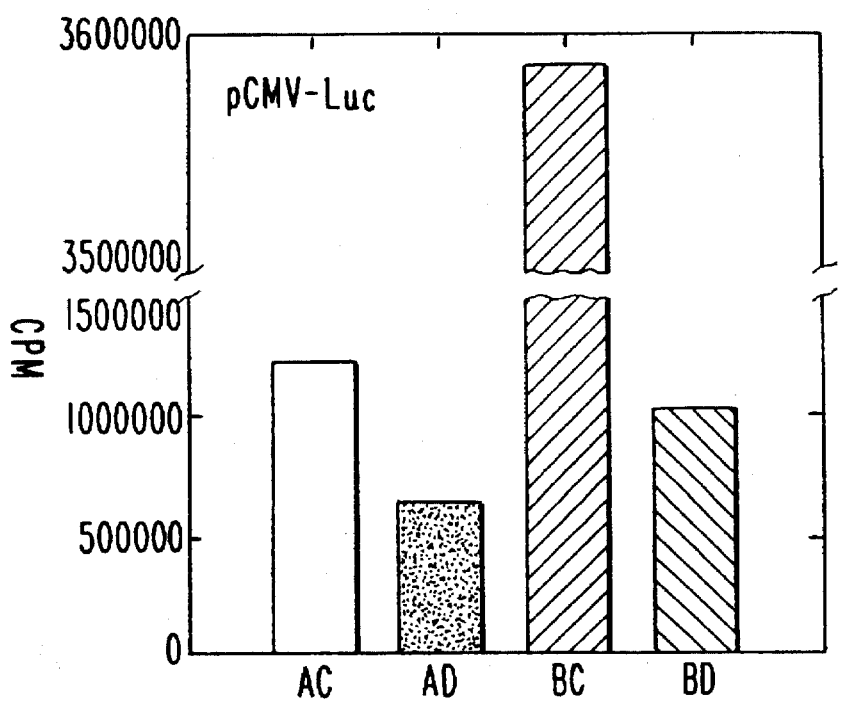
Figure 6:
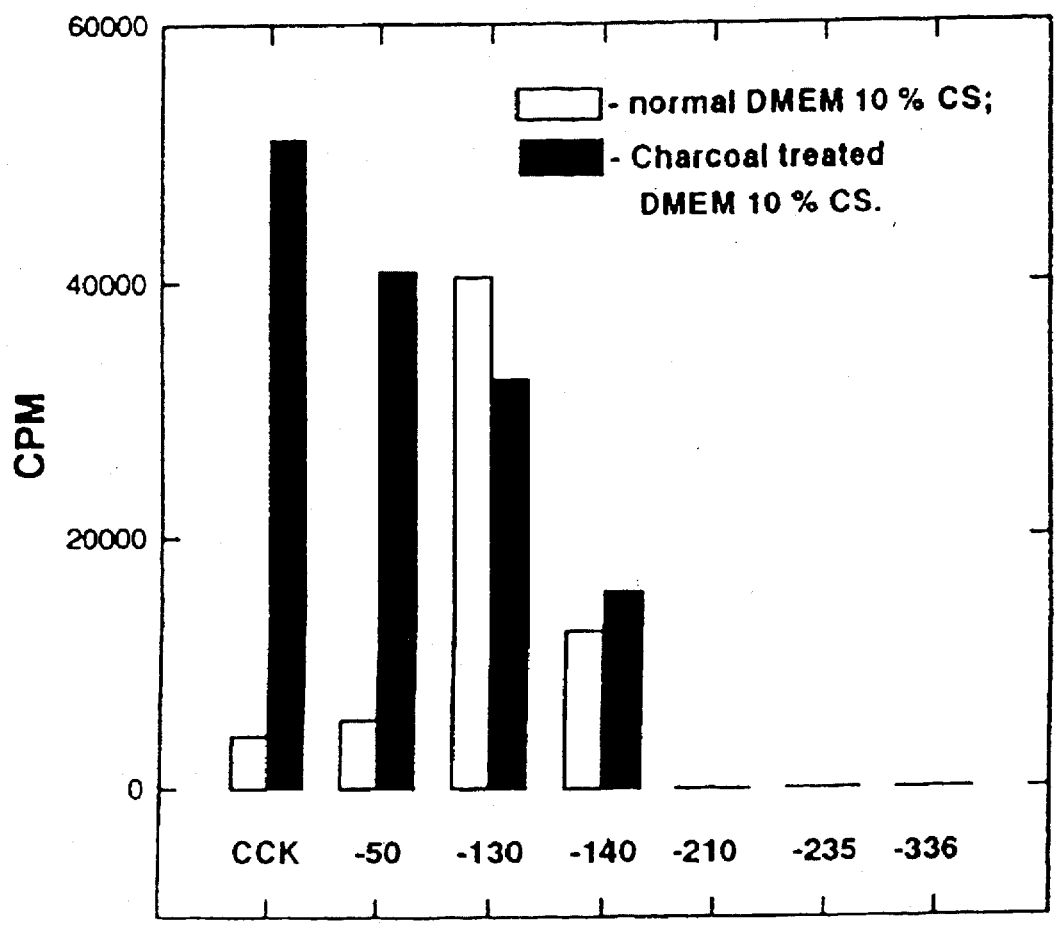
FIG. 6 is a bargraph showing the effect of the inhibitory component of calf serum on the expression of luciferase from CCK UER deletion plasmids in GH3 cells. Normal DMEM containing 10% calf serum is depicted by plain bars. Charcoal treated DMEM containing 10% calf serum is depicted by filled bars.
Figure 7A:
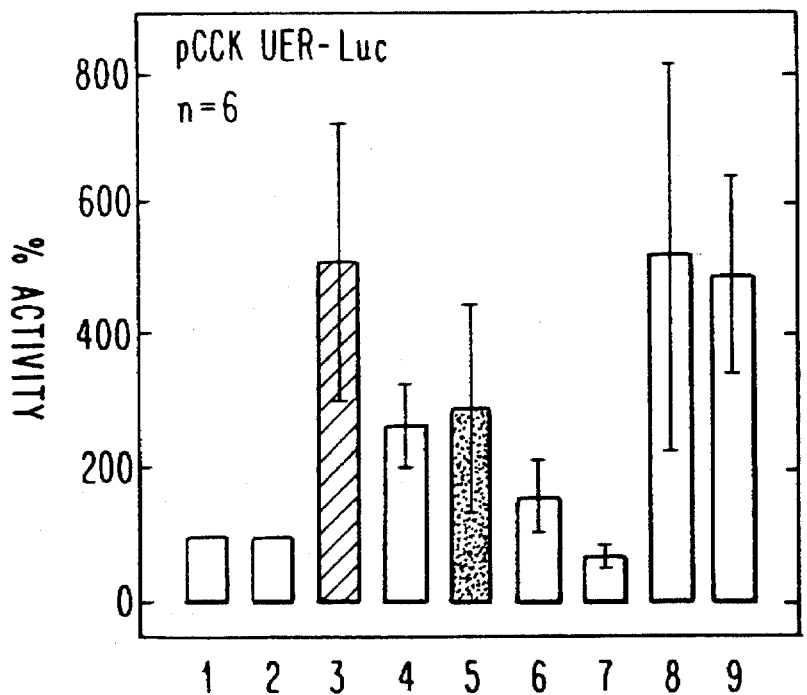
FIGS. 7A–7E provide bargraphs showing the effect of steroid hormones and transduction enhancer on luciferase activity expressed by pCCK UER-luc. Studies with the full 473 bp fragment are shown in FIG. 7A. Four nested deletions are also shown with distances 5' to the CAP site indicated.
Figure 7B:
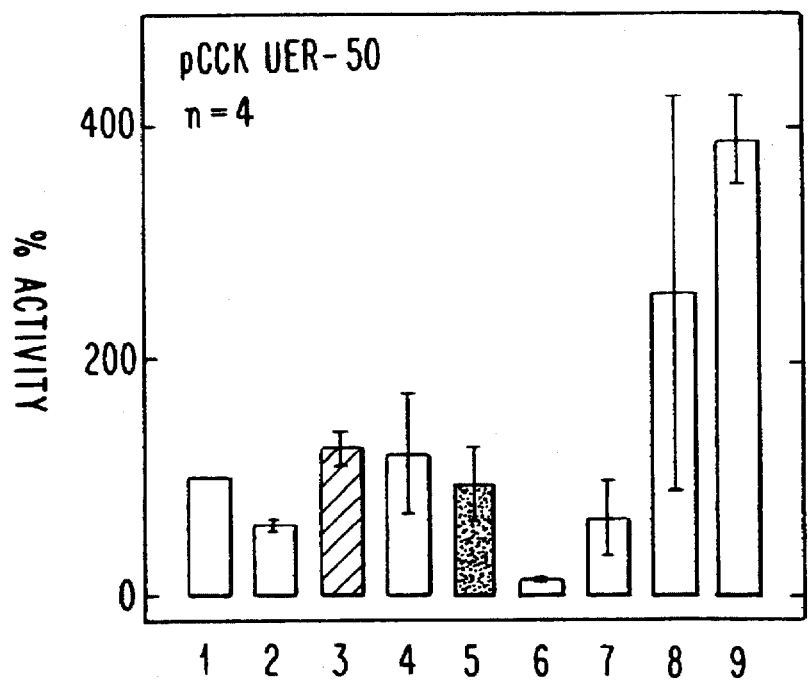
Figure 7C:
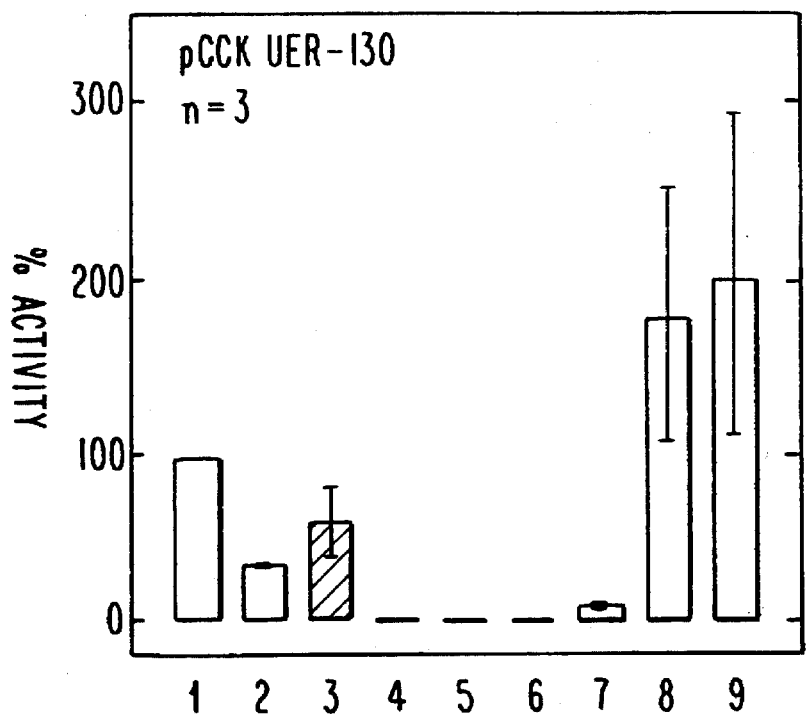
Figure 7D:
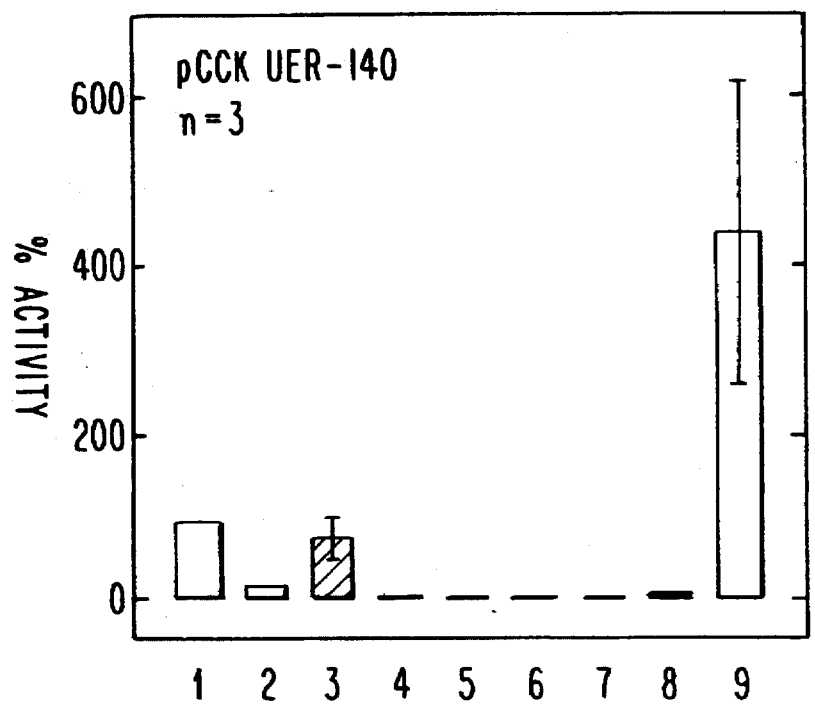
Figure 7E:
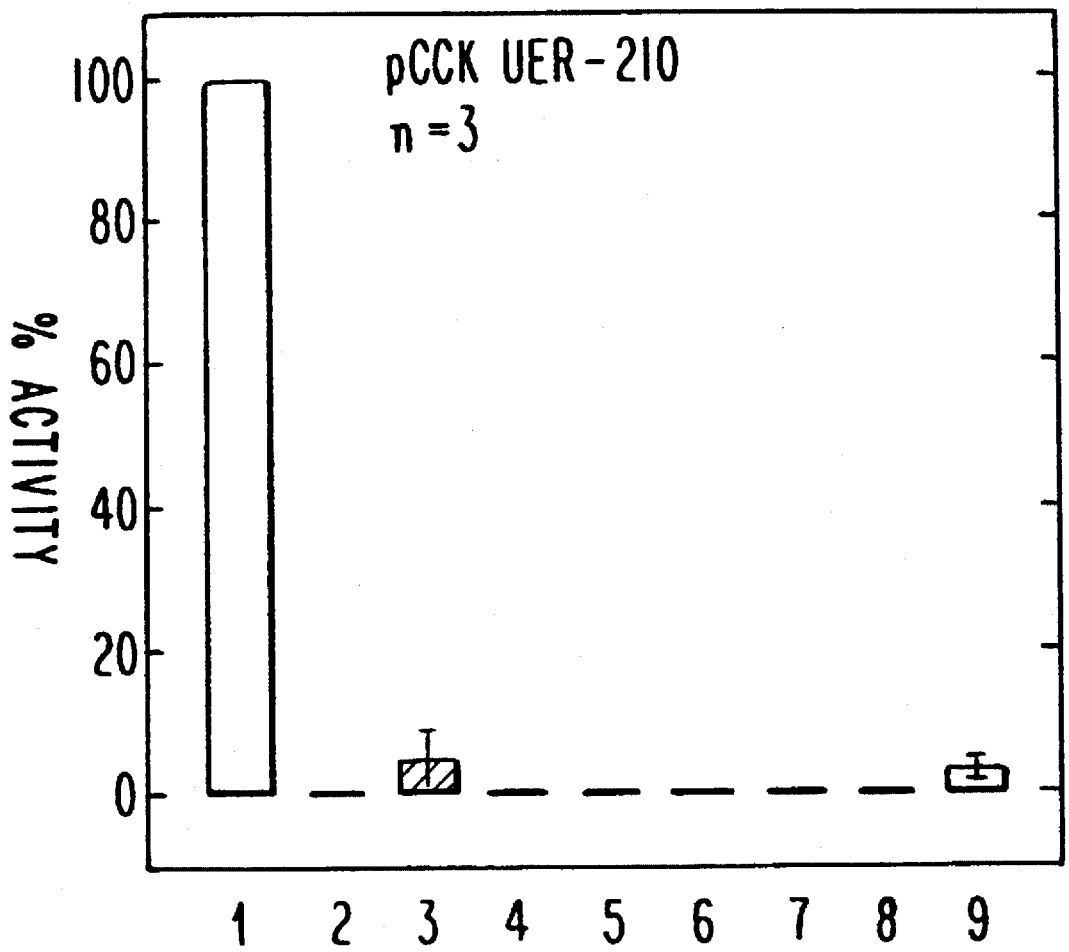

Inhibitory factors were found in calf serum that mapped to the 80 bp segment (-130 to -50 bp 5' to the CAP site). CMV is also inhibited by unstripped serum, but not to the same extent as CCK UER (FIG. 5, bottom). The components of unstripped calf serum which mediate CCK UER inhibition may comprise some steroids but remains to be further defined. However, stripping calf serum by adsorption to charcoal results in an order of magnitude increase in CCK UER signal (FIG. 5, top, and FIG. 6).

The effect of different classes of steroid hormones and transcriptional inductors has also been determined as well as mapping of DNA responsive regions. Steroid hormones and their receptors act as complex transcriptional factors (Cato, A. C. and Ponta, H. (1989) *Mol. Cell Biol.* 9:5324-5330). Immunohistochemical studies suggest that CCK levels in forebrain nuclei are regulated by gonadal steroids, particularly estrogens (Oro, A. E. et al. (1988) *Neuroendocrinology* 47:225-235; Simerly, R. B. and Swanson, L. W. (1987) *Proc. Nat'l Acad. Sci. USA* 84:2087-2091). In these experiments, it was determined that the androgen, 3,17 androstenedione, is the most powerful inducer, followed by the estrogen, 17b-estradiol, a gestagen, progesterone, and a glucocorticoid, corticosterone. The mineralocorticoid aldosterone does not induce CCK UER. Transduction enhancers, TPA (phorbol 12-myristate, 13-acetate) and forskolin are potent CCK inducers. TPA activation occurs in a 10 bp region (-140 to -130 5' to the CAP site). Inhibition with forskolin and TPA in combination is mediated by this same region, which contains AP-2 consensus recognition sequences. Only androstenedione and forskolin retain activity more than 210 bp 5' to the CAP site.

DNA vectors of the present invention were also successfully transfected, expressed and their reporter gene quantified in animals. Two promoters were evaluated in these experiments, the intact 400 bp CCK-UER and a construct wherein the first 130 bases, including the TATTA box 5' to the CAP site had been deleted (CCK-130). In these experiments, the selected gene was the luciferase reporter gene. The liposome used in these experiments was 3β[N', N'-dimethylaminoethane)carbomyl]cholesterol (DC-CHol) 1,2-dioleoyl-s,n glyceroethanolamine (DOPE). Fasted male rats were anesthetized and 5 to 10 µg of liposome-DNA complex were injected into the proximal duodenal wall or lumen or into the liver. Control animals were administered liposome alone. Animals were sacrificed 24 hours after treatment and tissues at and distant from the injection site were removed, processed and assayed. No luciferase activity was observed in the tissue from the control animals. Signal was detected in both CCK-UER and CCK-130 at the site of injection in both the duodenum and the liver. In the gut, signal was additionally detected distal to the injection site as far as the mid small bowel. By contrast, in the liver, signal was only detected in the region of injection. The fact that CCK-130 produces signal indicates that an additional start site in the distal upstream regulatory region is being utilized on the transfected DNA. Signal is detected both in regions where the CCK gene is produced as in the gut and where it is not produced as in the liver thus indicating that the transfected CCK promoter DNA is differentially regulated from the endogenous CKK gene. Accordingly, the vectors of the present invention are useful in delivering a selected gene to any cell, not just those cells which contain the specific tissue or organ promoter which has been incorporated in the vector. Detection distally along the gut demonstrates that luminally transported DNA is successfully transfected thus indicating that enteral, liposome transfected, eukaryotic DNA transfer can be achieved.

A principle advantage of this embodiment of the present invention is the relative ease of an oral or intraintestinal delivery route for gene delivery. In a preferred embodiment, the tissue specific promoter delivers the genes to the desired location, e.g., cells of the intestinal wall, where it is placed under endogenous hormonal regulation of expression. These intestinal cells then deliver the gene products directly into the blood stream. As such, this site of gene delivery is ideal for secretory peptides or proteins. As intestinal cells are regularly shed, a facile method of gene delivery would allow retransplantation on a regular basis. While this may seem to be a disadvantage for long-term stability of expression of gene products, regular shedding may be an advantage if toxicity or immune responses to delivered gene products arise. A schedule of expression followed by reduction to basal levels due to shedding and retransplantation, can reduce toxicity and allow immune tolerization. It also permits titration of the amount of the gene product to achieve therapeutic levels.

For this embodiment liposomes capable of surviving the stomach (e.g., by acid stable coatings used on tablets) can be formulated to allow ultimate delivery of encapsulated DNA vectors of the present invention into the duodenum where gene delivery has been demonstrated. However, as is well appreciated by those of skill in the art, the DNA vectors of the present invention can be delivered by various routes of administration in various biologically compatible solutions or pharmaceutically suitable delivery vehicles. Appropriate vehicles can be routinely selected in accordance with the tissue or organ specific promoter and the specific tissue or organ to be targeted and the selected gene to be transplanted. For example, since the CCK UER promoter is derived from a brain-gut peptide, the pCCK UER vector may be used to deliver regulated genes into the brain cells following intracerebroventricular injections or direct injection into specific regions of the brain. Such vectors are useful in diseases wherein a gene product defect produces pathology such as in Parkinsons Disease where there is a dopamine deficiency due to inadequate levels of tyrosine hydroxylase in the basal ganglia. In this embodiment, the DNA vector may be delivered in a different vehicle since protection from the stomach acid is not a concern. As has been demonstrated, however, a DNA vector comprising the CCK UER promoter can also be used to deliver a selected gene to a cell which does not naturally express the endogenous gene, such as the liver.

The present invention also provides a cellular and animal model system for evaluating agents that facilitate gene transplantation in the context of a relevant promoter/target tissue combination. For example, experiments were performed to determine the efficiency of several lipid compounds in transfecting a DNA vector of the present invention into cells. Agents which may be used to facilitate the transfection of DNA vectors may be compared and evaluated by transfecting a DNA vector containing an effective upstream enhancer region of a tissue or organ specific mammalian promoter of an endogenous gene and a selected gene with a selected agent into a selected cell line and comparing the levels of expression of the selected gene for each selected agent.

The present invention also provides a rapid, facile and reproducible in vitro system for evaluating compounds that might be transcriptional effectors or inhibitors of brain-gut promoters in a relevant cognate cell line. Compounds can be evaluated by transfecting a DNA vector containing an effective upstream enhancer region of a brain-gut mammalian promoter and a selected gene into a relevant cognate cell line in the presence of a compound to be evaluated. The level of expression of the selected gene in these cells in the presence of the compound is then compared to level of expression in cells without the compound to determine whether the compound may act as a transcriptional effector or inhibitor.

The following nonlimiting examples are provided to further illustrate the present invention.

EXAMPLES

Example 1: Cloning of the CCK UER

The promoter was subcloned into the reporter construct by sequential PCR amplification with Vent DNA polymerase (1 unit, New England Biolabs, Beverly, Mass.) and then repeated with Thermus aquaticus DNA polymerase (1 unit, Promega, Madison, Wis.). Sprague-Dawley rat genomic DNA (50 ng) was mixed with 1x PCR buffer for Taw and Vent polymerase respectively, 3 mM dNTPs, and 10 nmols of primers. The primer pair (upstream: 5'-ACCTAGTCTGTGAGGGTCCC-3' (SEQ ID NO: 1) and downstream: 5'-GGATCTGCCAGCCACTTACC-3' (SEQ ID NO: 2)) were custom designed from published rat CCK sequences (Deschenes, R. J. et al. (1984) *Proc. Nat'l Acad. Sci. USA* 81:726–730) and purchased from the Brookdale Center of Molecular Biology, Mt. Sinai School of Medicine, N.Y. Twenty-five amplification cycles of denaturation at 94° C. for 30 seconds, primer annealing at 57° C. (for Taq polymerase) and 60° C. (for Vent polymerase) for 60 seconds, and extension at 72° C. for 2 minutes (PTC-150 Thermocontroller, M. J. Research, Watertown, Mass.).

Ten microliters of the PCR end product were subjected to a 6% PAGE. Gels were stained with ethidium bromide and UV photographed. A 473 bp band was excised and eluted by incubation at room temperature in 50 ml of TE (10 mM Tris, 0.01 mM EDTA, pH 8.0; Sambrook et al. (1989) in *Molecular Cloning A Laboratory Manual*. Cold Spring Harbor Laboratory Press, Cold Spring Harbor, N.Y.) for 12 hours.

One microliter of this extract was ligated into pBL-Luc vector (see FIG. 2) at 12° C., overnight. DNA was isolated by the alkali-lysis method using Magic DNA purification Resin® (Promega, Madison, Wis.). Purified DNA was washed three times in TE buffer using a Centricoh-100 cartridge (Amicon Inc., Beverly, Mass.). All PCR fragments used in this study were sequenced. Cloning was repeated in separate experiments to confirm the sequences.

A series of 3' to 5' nested deletions were generated using exonuclease III digestion (Erase-A-Base Kit, Promega, Madison, Wis.). Aliquots were removed from the digestion mixture at 30 second intervals, quenched, filled and re-ligated. Six constructs (as shown in FIG. 1) were subsequently used in transient transfection assays. Fragments are identified by the number of bases digested 5' to the CAP site.

Example 2: Plasmid constructs

Fragments were cloned into the polylinker of pBluescript II KS M13 (Stratagene, La Jolla, Calif.). The primal construct, pBL-Luc has *P. pyralis* luciferase reporter gene (see FIG. 2). Of particular note are the two SV-40 poly-A stop codons located proximal to the multiple cloning site, and distal to the luciferase reporter. These stop codons reduce the background signal by two orders of magnitude. Four viral promoter-luciferase constructs and one CMV-b-galactosidase constructs were used to develop and validate the CCK UER assay.

Example 3: GH3 cell culture

Rat pituitary tumor GH3 cells (ATCC, Rockville, Md.) were plated in Dulbecco's modified Eagle's medium (DMEM) containing 10% calf serum (GIBCO/BRL, Gaithersburg, Md.) in 24-well (16 mm diameter) cell culture plates (Costar, Cambridge, Mass.), previously treated with 10 mg/ml poly-L-lysine (Sigma, St. Louis, Mo.) and washed twice with serum free DMEM. Cells were plated at a density of $0.5 \times 10^6$ cell/well and incubated for 24 hours at 37° C. in a humidified atmosphere of 5% $CO_2$ until 40–60% confluent.

Example 4: Cationic-liposome-mediated transfection

Figure 3A:
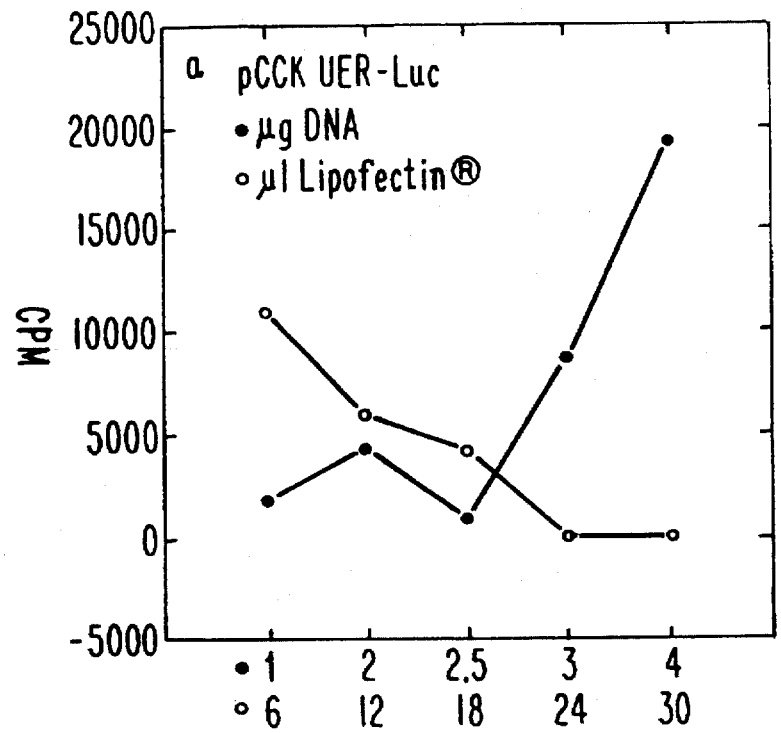
FIG. 3a and 3b provide the optimal conditions for transfections with pCCK UER luciferase (FIG. 3a) and pCMV b-galactosidase (FIG. 3b). Open circles show the effect of increasing volume of Lipofectin® and solid circles show the effect of increasing the amounts of DNA. As a result of these data, 2 mg of DNA and 6 mg of Lipofectin® (1 mg/ml) were used. Axes are CPM (count/min) and A420 (absorbance at 420 nm, 1 cm pathlength).
Figure 3B:
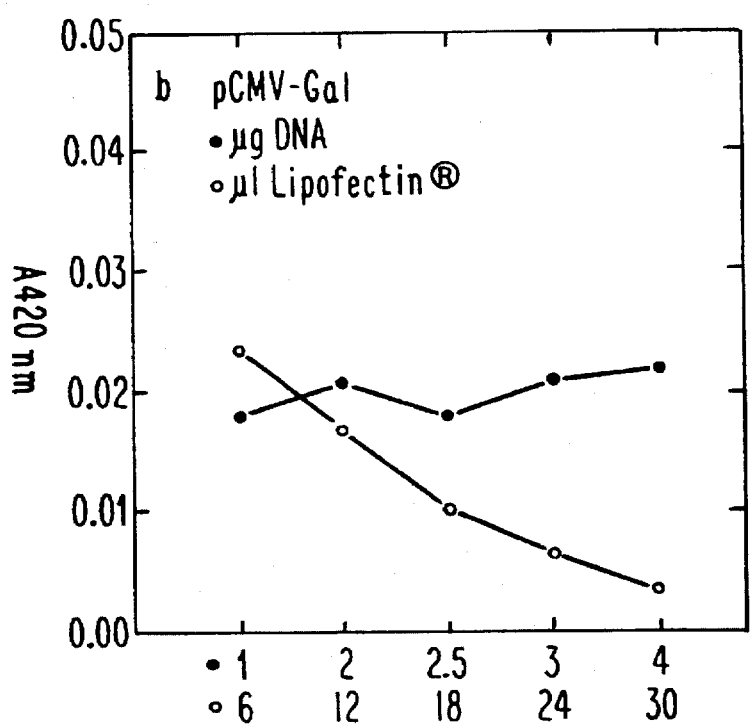

GH3 cells were transfected with reporter constructs (see FIG. 2). The optimal amounts of vectors and volume of Lipofectin® Reagent (GIBCO/BRL, Gaithersburg, Md.) were determined (see FIGS. 3a and 3b). Efficiency of pCCK UER-Luc was compared with a pCMV-Gal (see FIG. 3b). The DNA (2 ml)/Lipofectin® (6 ml) mixture was incubated at room temperature for 15 minutes. Cells were rinsed twice with 0.5 ml of serum-free DMEM and the DNA/Lipofectin® solution added. The cell/DNA/Lipofectin mixture was incubated for 6 hours at 37° C., 5% $CO_2$. The medium was removed and replaced with 0.5 ml of DMEM containing 10% charcoal-treated calf serum (100 ml calf serum was mixed with 2 g of charcoal for 90 minutes at 4° C. Stripping calf serum by adsorption to charcoal results in an order of magnitude increase in CCK UER signal (FIG. 5, top, and FIG. 6). The inhibitory factor is in the calf serum and not in the DMEM medium (FIG. 5, top-BC). Cells were harvested 24 hours later and assayed for luciferase and b-galactosidase activity.

Example 5: Luciferase assay

Cell extracts (20 ml) were assayed using a Luciferase Assay Kit (Promega, Madison, Wis.) and quantified in a Beckman LS7000 liquid scintillation counter (Beckman Instruments, Fullerton, Calif.) for 2 minutes. Assay sensitivity was determined using firefly luciferase (Boehringer-Mannheim, Indianapolis, Ind.) over a range of 0.001–10 fg. The limit of detection was determined to be 0.1 fg of luciferase.

Example 6: b-Galactosidase enzyme assay pCMV-Gal transfected cells were rinsed twice with PBS ($Mg^{2+}$ and $Ca^{2+}$ free) buffer and incubated with 300 ml of TEN buffer for 5 minutes at room temperature. Cells were scraped and centrifuged at 7000 g for 10 minutes at 4° C. Cell were resuspended in 150 ml of 0.25M Tris-HCl, pH 8.0, disrupted by three freeze-thaw cycles (dry ice and 37° C.), and the supernatants from a second centrifugation were assayed with a b-galactosidase Assay Kit (Promega, Madison, Wis.). The absorbance at 420 nm was measured by a Beckman DU-7 spectrophotometer (Beckman Instruments, Fullerton, Calif.).

Example 7: Transcriptional Efficiency of CCK

Figure 4:
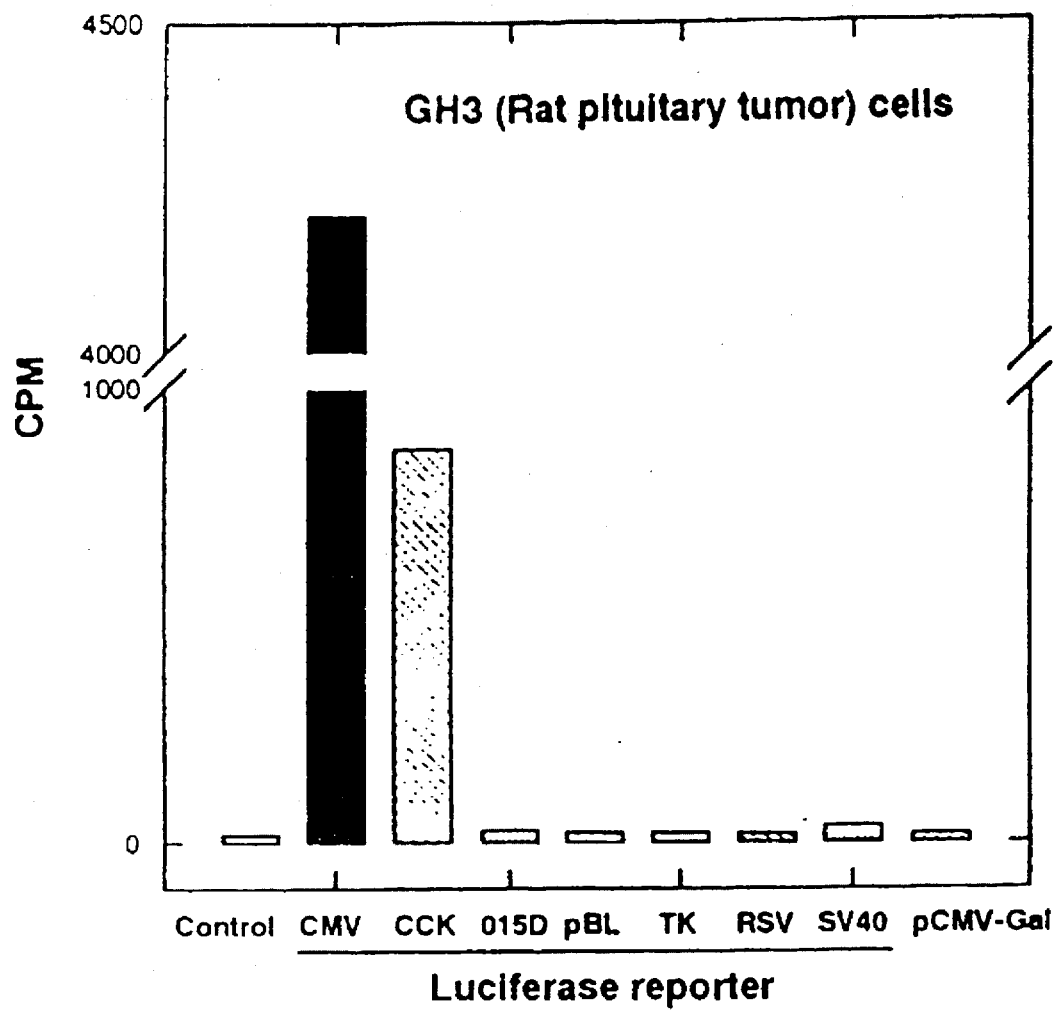
FIG. 4 provides a comparison of the transcriptional efficiency of CCK UER with other promoters. The *P. pyralis* luciferase gene was cloned downstream of different promoters, transfected into GH3 cells using the optimized Lipofectin® conditions described in FIG. 3 and extracts prepared. Promoters which were compared are from cytomegalovirus (CMV), SV40, Rous sarcoma virus (RSV), and herpes simplex thymidine kinase (TK). Negative controls include pBL-Luc cloning vector (control), pCMV-gal (control for endogenous luciferase) and p015D, a 566 bp nonsense fragment. Plasmid p015D has the upstream primer at both ends, and less than 7% homology with CCK UER.

To evaluate the transcriptional efficiency of CCK UER, seven vectors containing known promoters were compared (see FIG. 2). In these experiments CMV, the most powerful promoter, was 5-fold more potent than CCK UER. Three other well known promoters, SV40, Rous sarcoma virus, and herpes simplex thymidine kinase, have no activity in this GH3 cell assay (see FIG. 4). Negative controls included pBL-Luc, the primal construct, and p015D, a 566 bp nonsense fragment. Plasmid p015D has the upstream primer at both ends, and less than 7% homology with CCK UER.

Example 8: Effect of steroid hormones on CCK expression

To define the role of different steroid hormones on CCK expression in cell culture, five different classes of steroid hormones and two different transcriptional enhancers were evaluated. These included an estrogen (17b-estradiol, EST), a gestagen (progesterone, PR), an androgen (androst-4-ene-3,17-dione, AND), a glucocorticoid (corticosterone, CST), a mineralocorticoid (aldosterone, ALD), forskolin, and phorbol 12-myristate 13-acetate (TPA). Samples were reconstituted in water (EST, PR, CST, and ALD), in 70% methanol (AND), in dimethyl sulfoxide (forskolin, TPA) and further diluted in sterile water to a final concentration of 1 pmol/ml. In initial studies, 1 nM concentrations of steroids and 0.1 mM of forskolin and TPA were determined to be optimal for subsequent studies. Aqueous solutions (50 ml) of steroids, phorbol ester and forskolin were added to media following transfection. Fresh dilutions of transcriptional inducers were prepared for each transfection. Values from different experiments were normalized to the intact CCK UER activity (100%, see FIG. 7) and presented as the mean±1 SEM.

A gradient in steroid regulated expression of CCK UER promoter was observed. The most potent enhancer was androstenedione (FIG. 7, top panel, lane 3), followed by estradiol, progesterone and corticosterone. The mineralocorticoid aldosterone had no effect on expression (FIG. 7, panels 1 and 2, lanes 4–7). Inhibition by estradiol, progesterone and corticosterone occurs in an 80 bp segment between −50 and −130 bp 5' to the CAP site (FIG. 7, panel 3, lanes 4–6). Both signal transducers, phorbol ester (TPA) and forskolin induce expression until −130 bp have been deleted (FIG. 7, panel 4, lane 8). The two most potent activators, androstenedione and forskolin retain activity even when −210 bp have been deleted (FIG. 7, panel 5, lanes 3 and 9). The interaction between the two transcription enhancers, TPA and forskolin were evaluated with this system. In combination they inhibit each other until −130 bp have been deleted. Deletion of an additional 10 bp results in loss of this inhibition. TPA activity is lost in pCCK UER-140 (FIG. 7, panel 4, lane 8) and that forskolin is transcriptionally active in pCCK UER-210 (FIG. 7, panel 5, lane 9).

Example 9: Evaluation of cationic liposomal formulation for optimal transfection efficiency The efficiency of 8 lipid compounds in transfecting the CCK UER luciferase reporter gene into GH3 cells was monitored by luciferase expression as measured by luminescence. Compound 1 is Lipofectin® (Gibco-BRL, Gaithersburg, Md.). Compound 2, 1,2-dioleoyl-s,n glyceroethanolamine (DOPE), was prepared in accordance with well known procedures. Compounds 3 through 8 are dimethyldioctadecylammonium bromide (DDAB), 1,2-dimyristoyl-sn-glycero-3-ethyphosphocholine (DMePCh), 1,2-dioleoyl-3-trimethylammonium propane (DOTAPr), 1,2-distearoyl-3-trimethylammonium-propane (DSTAPr), 1,2-dimyristoyl-3-trimethylammonium-propane (DMTAPr), and 1,2-dipalmitoyl-3-trimethylammonium-propane (DPTAPr), respectively (Avanti Polar, Alabaster, Ala.). Compounds 2 through 8 all contained DC-Chol (3β[N',N'-dimethylaminoethane)-carbomoyl]cholesterol). Of all the compounds tested, transfection into GH3 cells is maximal when the hydrocarbon tail of the polar lipid has 14 fully saturated carbon atoms (DmePCh and DMTAPr). Transcriptional activity data is summarized in Table 1.

TABLE 1

| Cmpd # | Transfecting Lipid Compound | Carbon Atoms | RLU |
|---|---|---|---|
| 1 | Lipofectin ® | Mixed | 4714 |
| 2 | DOPE | 18:1 | 597 |
| 3 | DDAB | 16:0 | 1811 |
| 4 | DMePCh | 14:0 | 6536 |
| 5 | DOTAPr | 18:1 | 937 |
| 6 | DSTAPr | 18:0 | 531 |
| 7 | DMTAPr | 14:0 | 5512 |
| 8 | DPTAPr | 16:0 | 2255 |

Carbon atoms refers to the number per lipid tail of total versus unsaturated carbons. RLU refers to relative light units and is provided as a mean±SEM.

The CCK UER luciferase reporter gene was successfully transfected, induced and its reporter product quantified in GH3 cells. Of the compounds evaluated, transfection into GH3 cells is maximal when the hydrocarbon tail of the polar lipid has 14 fully saturated carbon atoms as in compound 4, DMePCh, and compound 7, DMTAPr.

Example 10: Tissue specific gene delivery via an enteral route

Two promoters were evaluated, the intact 400 bp upstream enhancer of the rat cholecystokinin gene (CCK UER) or the construct where the first 130 bases (including the TATTA box) 5' to the CPA site had been deleted (CCK UER-130). The liposome was 3β[N',N'-(dimethylaminomethane)carbamoyl]cholesterol (DC-CHol) 1,2-dioleoyl-s,n-glyceroethanolamine (DOPE).

Fasted male adult rats were anesthetized and 300 ml liposome (control) or liposome-DNA (5–10 mg) complex were injected into the proximal duodenal wall or lumen, or into the liver parenchyma. Following sacrifice at 24 hours, tissues at and distant from the injection site were excised, processed by homogenization, cell-free extracts prepared, and assayed for luciferase activity.

There was no luciferase activity in the control tissue. Signal was detected with both CCK UER and CCK UER-130 at the site of injection in both the duodenum and the liver. In the gut, signal was additionally detected distal to the injection site as far as the mid small bowel. By contrast, in the liver, signal was only detected in the region of injection.

What is claimed is:

1. A DNA vector comprising an effective upstream enhancer region of a gut/brain specific mammalian promoter and a selected gene wherein said effective upstream enhancer region of a gut/brain specific mammalian promoter is selected from the group consisting of gastrin, somatostatin, vasoactive intestinal polypeptide, neuropeptide Y gene, cholecystokinin upstream enhancer region (CCK UER) and CCK UER 130.

* * * * *

UNITED STATES PATENT AND TRADEMARK OFFICE
CERTIFICATE OF CORRECTION

PATENT NO. : 5,681,744

DATED : Oct. 28, 1997

INVENTOR(S) : Greenstein

It is certified that error appears in the above-indentified patent and that said Letters Patent is hereby corrected as shown below:

On the title page: Item [54] and Column 1, line 2, please delete "heterologus" and insert therefor --heterologous--.

At col 1, line 41, please delete "etal." and insert therefor --et al.--.

Signed and Sealed this

Twenty-eighth Day of April, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
      ( A ) LENGTH: 20
      ( B ) TYPE: Nucleic Acid
      ( C ) STRANDEDNESS: Single
      ( D ) TOPOLOGY: Linear ( i v ) ANTI-SENSE: No ( x i ) SEQUENCE DESCRIPTION: SEQ ID NO: 1:

ACCTAGTCTG TGAGGGTCCC                    20

( 2 ) INFORMATION FOR SEQ ID NO: 2:

( i ) SEQUENCE CHARACTERISTICS:
      ( A ) LENGTH: 20
      ( B ) TYPE: Nucleic Acid
      ( C ) STRANDEDNESS: Single
      ( D ) TOPOLOGY: Linear ( i v ) ANTI-SENSE: No ( x i ) SEQUENCE DESCRIPTION: SEQ ID NO: 2:

GGATCTGCCA GCCACTTACC                    20